(12) United States Patent
Hardman et al.

(10) Patent No.: US 8,529,837 B2
(45) Date of Patent: Sep. 10, 2013

(54) SYSTEM AND METHOD FOR DETECTING SPECIFIC BINDING REACTIONS USING MAGNETIC LABELS

(75) Inventors: Clayton M. Hardman, Orangevale, CA (US); Sanjay R. Mishra, Germantown, TN (US)

(73) Assignee: Biomag Corp., Orangevale, CA (US)

( * ) Notice: Subject to any disclaimer, the term of this patent is extended or adjusted under 35 U.S.C. 154(b) by 174 days.

(21) Appl. No.: 11/500,140

(22) Filed: Aug. 7, 2006

(65) Prior Publication Data
US 2008/0032422 A1    Feb. 7, 2008

(51) Int. Cl.
*G01N 15/06* (2006.01)

(52) U.S. Cl.
USPC .......... 422/68.1; 436/518; 436/164; 436/165; 436/807; 436/524; 436/526; 435/7.1; 435/283.1; 435/288.7; 435/287.1; 435/287.2

(58) Field of Classification Search
USPC ................. 436/518, 524, 525, 526, 164, 165, 436/807; 435/7.1, 283.1, 287.2, 288.1, 288.7, 435/287.1; 422/50, 68.1, 82.05, 82.09, 400
See application file for complete search history.

(56) References Cited

U.S. PATENT DOCUMENTS

| | | | | |
|---|---|---|---|---|
| 4,171,912 A | * | 10/1979 | Ito et al. | 356/320 |
| 4,208,129 A | * | 6/1980 | Spencer | 356/425 |
| 4,377,340 A | * | 3/1983 | Green et al. | 356/237.3 |
| 4,725,140 A | * | 2/1988 | Musha | 356/336 |
| 4,916,081 A | * | 4/1990 | Kamada et al. | 436/526 |
| 5,056,888 A | * | 10/1991 | Messerly et al. | 385/123 |
| 5,599,668 A | * | 2/1997 | Stimpson et al. | 435/6 |
| 6,254,830 B1 | * | 7/2001 | Pivarnik et al. | 422/82.07 |
| 2001/0030982 A1 | * | 10/2001 | Maki | 372/26 |
| 2006/0240411 A1 | * | 10/2006 | Mehrpouyan et al. | 435/5 |

* cited by examiner

*Primary Examiner* — Melanie Y Brown
(74) *Attorney, Agent, or Firm* — Philip M. Weiss; Weiss & Weiss

(57) ABSTRACT

A system and method for detecting specific binding reactions using magnetic labels.

11 Claims, 3 Drawing Sheets

SYSTEM AND METHOD FOR DETECTING SPECIFIC BINDING REACTIONS USING MAGNETIC LABELS

FIELD OF THE INVENTION

The present invention relates to a system and method for detecting specific binding reactions using magnetic labels.

BACKGROUND OF THE INVENTION

There have been significant developments in techniques for measuring immunological substances, such as, anti-bodies, hormones, medicines, drugs, and various other components in blood, measurements of the smallest possible amounts. The primary techniques used to detect these substances are based on labeling, where primary ligands with labels are attached to the substance of interest. The detection of these labels conveys the presence or absence of the target substance. A wide variety of labeling techniques is used for this purpose such as chemical labels, radiolabels, dye labels, etc. However, these techniques are inherently expensive, non-portable, and have environmental side effects.

U.S. Pat. No. 4,313,734 relates to a method, test kit, and labeled component for the detection and or determination of one or more components of the reaction between a specific binding protein and the corresponding bindable substance. One or more labeled components are used that are obtained by coupling particles of a dispersion of a metal, metal compound, or polymer nuclei, coated with a metal or metal compound, having a particle size of at least 5 nm, directly or indirectly to the desired component of the reaction.

U.S. Pat. No. 7,005,108, and patent publication numbers 2003/0192780 and 2006/0096866 relate to methods and insulator electrode devices for performing electrochemical reactions. The devices consist of high specific surface area electrodes based on a channeled conducting base material but has been coated with an organic or inorganic insulating film or multiple layers of such films. The chemical reactions are exemplified by exciting one or several label compounds into an excited state which is spontaneously de-excited by emission of ultraviolet, visible or infrared lights in aqueous solution.

U.S. patent publication number 2003/0124733 relates to a method for preserving a sample. The device include microarrays, slides and membranes. The preservation is achieved by applying a coating composition to a sample or sample device and curing the coating composition.

U.S. Pat. No. 4,725,140 relates to a coherent light beam made incident upon a cell via a polarizer. In the cell is contained a reaction liquid consisting of fine magnetic particles having an anti-body coated thereon and a sample containing an antigen which is specifically reacted with the anti-body on the particles. The particles are rotated in the reaction liquid by means of alternating magnetic fields having a frequency and generated by coils arranged beside the cell. Light scattered by the particles is made incident upon a photo detector via polarizer whose polarization plane is perpendicular to that of the analyzer. An output signal from the photo detector is synchronously detected by means of a reference signal having a frequency. Then a synchronously detected output signal represents an amount of the antigen contained in the sample.

U.S. Pat. No. 4,267,509 relates to a magneto-optical device, which is responsive to magnetic fields by means of a Tyndall Effect in a particular direction exhibited by aligned magnetic colloidal particles suspended in an illuminated liquid medium. The liquid medium is contained in a transparent vessel and has magnetic particles in a very low density, such that the liquid is substantially transparent to the naked eye. A light source is positioned to illuminate the liquid medium and a light-sensing device or photocell is positioned to receive light scattered by the magnetic particles. The light-sensing device is positioned at a predetermined angle from the paraxial direction of the light source. All colloidal solutions, when illuminated by a beam of light, exhibit the Tyndall Effect, i.e. a visible scattering of light by colloidal particles. When the magnetic colloidal solution of this device is brought into the presence of a magnetic field, the magnetic particles become aligned, causing the directed scattering of light called herein the Directional Tyndall Effect, which scattering can be detected by the photocell. In order to minimize the effects of surrounding light, the vessel containing the liquid medium can be enclosed in an opaque container with the photocell and light source mounted in appropriate apertures. For use in varying applications, two photocells can be provided, with the photocells and light source in an orthogonal arrangement.

U.S. Pat. No. 6,855,556 relates to compositions of mutated binding proteins containing reporter group, analyte biosensor devices derived therefrom, and their use as analyte biosensor both in vivo and in vitro. The invention provides a glucose biosensor for in vivo or in vitro use having at least one mutated binding protein and at least one reporter group attached thereto such that the reporter group provides a detectable and reversible signal change when the mutated binding protein is exposed to varying glucose concentrations, wherein the detectable and reversible signal change is related to the varying concentrations.

U.S. Pat. No. 4,812,767 relates to an optical apparatus using a strong magneto-birefringence of magnetic fluid. An external magnetic field is applied in the perpendicular direction to the propagation of the light beam, making the magnetic fluid thin film possess a birefringence property. The apparatus can be used for detecting a magnetic field and can be used as a magnetic field sensor and transformer.

U.S. Pat. No. 5,333,495 relates to a method and apparatus for detecting a photo acoustic signal which includes the steps of modulating the intensity of light obtained from a light source at a predetermined modulation frequency, exciting a specimen by directing the intensity-modulated light onto the specimen. This generates a photo acoustic effect in the specimen.

U.S. Pat. No. 6,437,563 relates to a method and apparatus for measuring combinations of magnetic particles combined by analytes whose amount or other characteristic quality is to be determined.

SUMMARY OF THE INVENTION

The present invention relates to a magneto-optical technique for immunological analysis using magnetic labeling. It is an object of the present invention for the method to be inexpensive and measurements to be performed automatically within a relatively short period of time.

The method of measuring an immunological reaction is comprised of the following steps:
1) Projecting radiation into a reaction liquid containing at least antigen-antibody.
2) Detecting scattered radiation by suspended magnetic particles.
3) Differentiating between specific and non-specifically bound articles suspended in an illuminated liquid medium.

The present invention is based on the Tyndall Effect. In particular, directional scattering exhibited by aligned magneto colloidal particles suspended in an illuminated liquid medium.

It is an object of the present invention to provide a very accurate and inexpensive method for detecting specific binding reactions using magnetic labels contrary to the techniques available in the market based specifically on radio-labeling.

According to the invention, a method of measuring a specific binding reaction comprises the following steps:

Projecting light (polarized/unpolarized) light on a transparent cell containing a pair of substances of interest and magnetic particle coated with specific ligand. Aligning the pair of substances in the external magnetic field. Measuring scattered light from the aligned magnetic particles using a photo detector. The direction of incident light, magnetic field, and detector is orthogonal to each other to detect maximum scattered radiation (Tyndall effect).

All colloidal solutions, when illuminated by a beam of light, exhibit the Tyndall Effect, i.e., a visible scattering of light by colloidal particles. When the magnetic colloidal solution of this device is brought into contact with the external magnetic field, the magnetic particles align in the direction of the field, causing a highly directional scattering of light known as Directional Tyndall Effect. This scattered light is highly place polarized.

Unpolarized light emitted from a light source is projected onto a cell, which contains a reaction liquid consisting of sample and fine particles made of magnetic material. The light can be incident on the reaction cell using fiber optic cable and a collimator. The reaction fluid is kept in an opaque cell. It is an object of the present invention for the cell walls to be coated internally to minimize the effect of light scattering from the interior of the cell. It is an object of the present invention for the housing to have two coils, which are continuous with each other but are separated by a distance equal to their radius. Thus they form Helmoltz coils and the magnetic field in the region between them is uniform. The Helmoltz coil is placed perpendicular to the direction of incident light and the photo detector. The magnetic particles are coated with specific antibody or antigen, which attaches to the sample to be analyzed. When the magnetic field is applied via a Helmoltz coil, the particles align along the direction of the external field. The scattered light from these aligned particles is highly plane polarized and directional in accordance with the Tyndall effect. The scattered light is once again collimated and transported to the detector via fiber optic cable or via a collimator. The scattered light is then detected by photo detectors arranged perpendicular to both direction of incident light and the magnetic field.

It is an object of the present invention to place an analyzer in between the reaction cell and the photo detector, which allows only one component of light to pass up to the detector. This set up differentiates the light scattered by agglutinated versus non-agglutinated particles.

It is an object of the present invention to use a separate analyzer, a fiber optics specifically designed to allow one component of light to pass through, thus acting as an analyzer and collimator. It is an object of the present invention to minimize any temperature variation in the incident intensity the photo detector current is normalized with the incident light.

It is an object of the present invention for the direction of light, magnetic field, and detection direction to be orthogonal in order to observe maximum Tyndall Effect.

The magnetic field is pulsed at a sinusoidal frequency f. Under the influence of the external magnetic field ferromagnetic particles will align along the direction of external magnetic field.

Since non-agglutinated particles are spherical and have optical isotrophy, they are polarized in the same direction as a vibrating direction of an electric field vector of electromagnetic wave of incident light. As a result light scattered by the non-agglutinated particles is linearly polarized. When the antibody-antigen reaction takes place, particles are agglutinated to each other. The configuration of agglutinated particles is no longer spherical and hence has an optical anisotropy. When the light is scattered by the agglutinated particles having optical anisotropy the scatted light has different polarization component than the polarization component of the light scattered by the non-agglutinated particles. This difference in the scattered intensity will give direct evidence of presence or absence of antibody-antigen pair present in the liquid.

According to the present invention, both non-agglutinated and agglutinated particles are moved by an external magnetic field. The external magnetic field is perpendicular to the direction of the incident light, thus aligning particles in a plane perpendicular to the plane of incident light. The polarization of light scattered by spherical non-agglutinated particles will have plane polarization. However, the polarization of light scattered by agglutinated particles is rotated in accordance with the rotation of the agglutinated particles. If a light analyzer is placed in the path of scattered light towards the detector such that plane of the analyzer is identical to the polarization plane of the scattered light, the light scattered by the non-agglutinated particles is made incident upon the photo detector along with the light scattered by the agglutinated particles. On the contrary, when the polarization plane of the analyzer is made perpendicular to the polarization plane of the scattered light only a part of the light scattered by the agglutinated particles is made incident upon the photo detector.

It is an object of the present invention for the polarizing plane of analyzer to be kept perpendicular to the plane of polarization of scattered light from non-agglutinated particles. When antibody-antigen reaction does not take place, the particles are non-agglutinated thus spherical particles will have optical isotropy, which linearly polarizes the scattered light. Thus, the scattered light is not passed through the analyzer whose principle axis is perpendicular to the plane of linearly polarized light. However, the agglutinated particles show optical anisotropy and thus the scattered light will not be linearly polarized. As a result, some component of the scattered light will be transmitted through the analyzer and to the photo detector.

It is an object of the present invention for the Tyndall Effect to be increased substantially by using a linearly polarized source instead of an unpolarized light source. It is an object of the present invention to use an additional polarizer in front of an ordinary light source. Thus, light transmitted through the polarizer is linearly polarized which is then incident on the reaction cell. This arrangement greatly enhances the intensity of the linearly polarized scattered light of the background due to unwanted scattering which is substantially reduced.

It is an object of the present invention to increase signal to noise ratio, by using two photodiodes. The two photodiodes are placed perpendicular to the direction of light and the magnetic field. The photo detector is placed parallel to the direction of incident light. When the magnetic field is applied maximum scattering of light will take place along +−Z-axis. In this situation, two detectors detect maximum scattered intensity while a third detector records a minimum. The current of these photodiode can be summed to improve S/N ratio.

It is an object of the present invention to use any ferromagnetic colloidal solution such as Fe, Co, Ni. The size and density of the particles can be selected to maximize the sensitivity. The size of the particles is not very critical as long as particles are smaller than the wavelength of the light used. It is an object of the present invention for the size of the particle to be 0.05 micron to 0.1 micron. The bigger size particles will only reflect light instead of scattering it and would not provide Directional Tyndall effect. Also, larger size particles will sediment thus prohibiting colloidal suspension. The outer surface is coated with antigen or antibody.

It is an object of the present invention for the detector to be a photodiode, photo multiplier tube, CCD, but not limited to all of these, can be employed to detect scattered light. It is an object of the present invention for the photo detector current to be directly fed to the electronics.

A hand held embodiment of the above device can be fabricated using optical fibers and CCD chip. The plane polarized light can be focused on a reaction cell using fiber optic. A CCD chip placed perpendicular to the both; direction of magnetic field and the incident light will detect the intensity of the scattered light.

It is an object of the present invention for the device to be used with an unpolarized source as it is based on the Tyndall Effect. It is an object of the present invention for the device to be used with a polarized source to increase sensitivity. It is an object of the present invention for the device to greatly enhance the photo detector response as maximum scattering intensity is detected in this geometry.

DETAILED DESCRIPTION OF THE INVENTION

Figure 1:
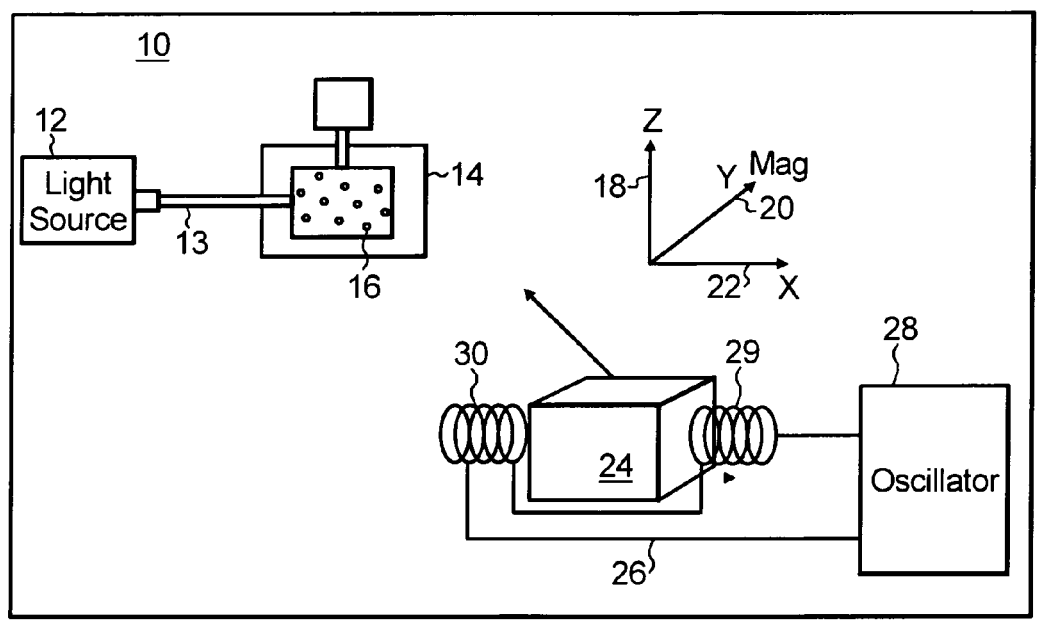
FIG. 1 is a schematic drawing showing the construction of a magnetic binding reaction measuring method and system.

FIG. 1, is a schematic drawing showing principle of construction of magnetic binding reaction measuring method and system. Unpolarized light emitted from a light source is projected onto a cell, which contains a reaction liquid consisting of sample and fine particles made of magnetic material. The light can be incident on the reaction cell using fiber optic cable and a collimator. The reaction fluid is kept in an opaque cell. The cell walls are coated internally to minimize the effect of light scattering from the interior of the cell. The housing also has two coils, which are continuous with each other but are separated by a distance equal to their radius. Thus they form Helmoltz coils and the magnetic field in the region between them is uniform. The Helmoltz coil is placed perpendicular to the direction of incident light and the photo detector, the vectorial configuration of the system is shown in FIG. 1. The magnetic particles are coated with specific antibody or antigen, which attaches to the sample to be analyzed. When the magnetic field is applied via Helmoltz coil, the particles align along the direction of external field. The scattered light from these aligned particles is highly plane polarized and directional in accordance with the Tyndall effect. The scattered light is once again collimated and transported to the detector via fiber optics cable or via a collimator. The scattered light is then detected by photo detectors arranged perpendicular to both direction of incident light and the magnetic field. An analyzer can be placed in between the reaction cell and the photo detector, as shown in FIG. 2, which allows only one component of light to pass up to the detector. This set up differentiates the light scattered by agglutinated versus non-agglutinated particles. Instead of using a separate analyzer, a fiber optics is specifically designed to allow one component of light to pass through, thus acting as an analyzer and collimator. In order to minimize any temperature variation in the incident intensity the photo detector current is normalized with the incident light as shown in FIG. 3a. The direction of light, magnetic field, and detection direction have to be orthogonal in order to observe maximum Tyndall Effect, see FIG. 1.

The magnetic field is pulsed at a sinusoidal frequency f. Under the influence of the external magnetic field ferromagnetic particles will align along the direction of external magnetic field.

Since non-agglutinated particles are spherical and have optical isotrophy, they are polarized in the same direction as a vibrating direction of an electric field vector of electromagnetic wave of incident light. As a result light scattered by the non-agglutinated particles is linearly polarized. When the antibody-antigen reaction takes place, particles are agglutinated to each other, the configuration of agglutinated particles is no longer spherical and hence has an optical anisotropy. When the light is scattered by the agglutinated particles having optical anisotropy the scatted light has different polarization component than the polarization component of the light scattered by the non-agglutinated particles. This difference in the scattered intensity will give direct evidence of presence or absence of antibody-antigen pair present in the liquid.

According to the present invention, both non-agglutinated and agglutinated particles are moved by an external magnetic field. The external magnetic field is perpendicular to the direction of the incident light, thus aligning particles in a plane perpendicular to the plane of incident light. The polarization of light scattered by spherical non-agglutinated particles will have plane polarization. However, the polarization of light scattered by agglutinated particles is rotated in accordance with the rotation of the agglutinated particles. If a light analyzer is placed in the path of scattered light towards the detector such that plane of the analyzer is identical to the polarization plane of the scattered light, the light scattered by the non-agglutinated particles is made incident upon the photo detector along with the light scattered by the agglutinated particles. On the contrary, when the polarization plane of the analyzer is made perpendicular to the polarization plane of the scattered light only a part of the light scattered by the agglutinated particles is made incident upon the photo detector.

In an embodiment, the polarizing plane of the analyzer is kept perpendicular to the plane of polarization of scattered light from non-agglutinated particles. When antibody-antigen reaction does not take place, the particles are non-agglutinated thus spherical particles will have optical isotropy, which linearly polarizes the scattered light. Thus, the scattered light will not be passed through the analyzer whose principle axis is perpendicular to the plane of linearly polarized light. However, the agglutinated particles show optical anisotropy and thus the scattered light will not be linearly polarized. As a result, some component of the scattered light will be transmitted through the analyzer and to the photo detector.

Figure 2A:
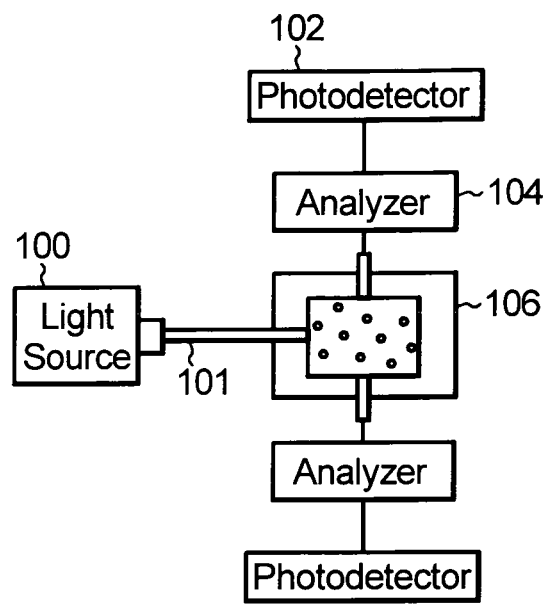
FIG. 2a is a schematic drawing showing the construction of a magnetic binding reaction measuring method and system.
Figure 3A:
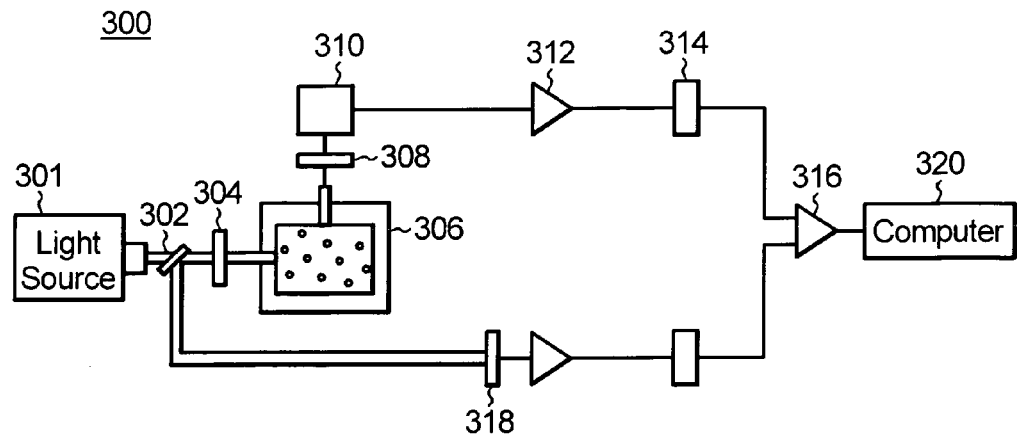
FIG. 3a is a schematic drawing showing the construction of a magnetic binding reaction measuring method and system.
Figure 3B:
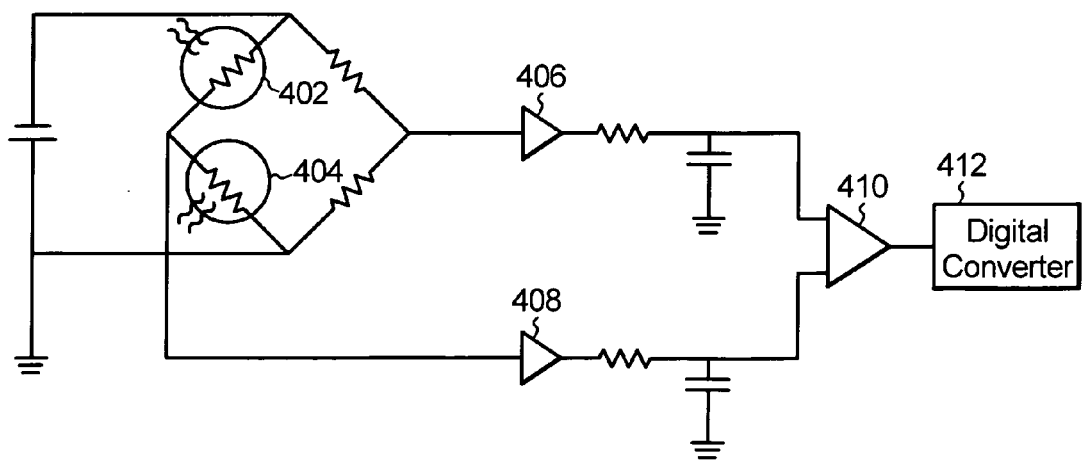
FIG. 3b is a schematic drawing showing the construction of a magnetic binding reaction measuring method and system.

The Tyndall Effect can be increased substantially by using a linearly polarized source instead of an unpolarized light source as shown in FIGS. 2a and 3b. Instead, one can also use an additional polarizer in front of an ordinary light source. Thus, light transmitted through the polarizer will be linearly polarized which is then incident on the reaction cell. This arrangement greatly enhances the intensity of the linearly polarized scattered light of the background due to unwanted scattering which is substantially reduced.

In order to increase signal to noise ratio, two photodiode can be placed as shown in FIG. 3b. Two photodiodes A and B are placed perpendicular to the direction of light and the magnetic field. The photo detector C is placed parallel to the direction of incident light. When the magnetic field is applied maximum scattering of light will take place along +−Z-axis. In this situation, detector A and B will detect maximum scattered intensity while detector C will record a minimum. The current of these photodiode can be summed to improve S/N ratio.

Any ferromagnetic colloidal solution such as Fe, Co, Ni can be used in the present embodiment. The size and density of the particles can be selected to maximize the sensitivity. The size of the particles is not very critical as long as particles are smaller than the wavelength of the light used. The preferred size of particle is 0.05 micron to 0.1 micron. The bigger size particles will only reflect light instead of scattering it and would not provide Directional Tyndall effect. Also, larger size particles will sediment thus prohibiting colloidal suspension. The outer surface is coated with antigen or antibody.

Any kind of detector such as photodiode, photo multiplier tube, CCD, but not limited to all of these, can be employed to detect scattered light. The photo detector current can be directly fed to the electronics as shown in FIG. 3a or 3b.

A hand held embodiment of the above device can be fabricated using optical fibers and CCD chip. The plane polarized light can be focused on a reaction cell using fiber optic. A CCD chip placed perpendicular to both direction of magnetic field and the incident light will detect the intensity of the scattered light.

The present invention can be used with an unpolarized source as it is based on the Tyndall Effect. In a preferred embodiment, a polarized source is used as it increases sensitivity. The Tyndall Effect geometry of the present invention greatly enhances the photo detector responses as maximum scattering intensity is detected in this geometry.

FIG. 1 shows a device 10 where unpolarized light is emitted from a light source 12 through an optical fiber 13 into a reaction cell 14. The reaction cell 14 contains a reaction liquid consisting of antigen-antibody ferromagnetic particles 16. The vectorial configuration of the system is shown as scattered light is shown on the z axis 18, the magnetic field is shown on the y axis 20 and the light is shown on the x axis 22. A source for current is provided for the device by an oscillator 28. The housing has two coils 29 and 30. Light 24 is shown in the reaction cell 14. The oscillator provides the current source for the electromagnet 26.

FIG. 2a shows the device having a light source 100 wherein the light travels through optical fiber 101. The device has a photodetector 102, which detects the scattered light and an analyzer 104 connected to the reaction cell 106. The analyzer 104 allows only one component of light to pass up to the detector 102.

Figure 2B:
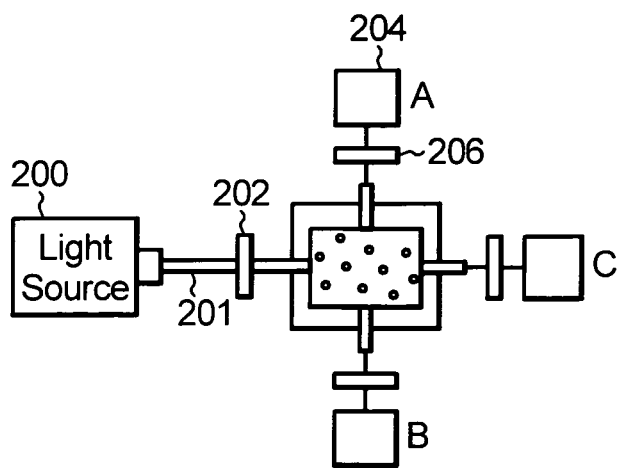
FIG. 2b is a schematic drawing showing the construction of a magnetic binding reaction measuring method and system.

FIG. 2b shows the device having a light source 200 wherein the light travels through optical fiber 201. Optical fiber 201 has a polarizer 202 attached to it. The device further comprises a photodetector 204 and analyzer 206.

FIG. 3a shows a device 300 having a light source 301, wherein light travels through an optical fiber 302. The optical fiber has a polarizer 304 attached to it. Light travels to the reaction cell 306. The light after passing through the reaction cell 306 then passes through an analyzer 308 to a photodetector 310. From the photodetector 310, a signal is passed through a reamplifier 312, a low pass filter 314 and a difference amplifier 316. The information is then sent to a computer 320. The light that does not pass through the polarizer and reaction cell passes through a photoresistor 318.

FIG. 3b shows two photodiodes. FIG. 3b shows a reference 402 and a detector 404. The system also has a reamplified 406 and a low pass filter 408. The signal then passes to the different amplifier 410 and then to an analog to digital converter 412.

The invention claimed is:

1. A system for measuring an immunological reaction comprising:
   a light source which emits unpolarized light from an optical fiber into a reaction cell;
   said reaction cell comprising a reaction liquid comprising antigen-antibody ferromagnetic particles;
   said reaction cell comprising a cell wall which is coated internally to minimize light scattering from interior of said cell;
   a source for current;
   a photodetector arranged perpendicular to both direction and incident of light and magnetic field.

2. The system of claim 1 further comprising two coils which are separated by a distance equal to their radius.

3. The system of claim 1 further comprising an analyzer placed between said reaction cell and said photo detector.

4. The system of claim 1 further comprising a reamplifier.

5. The system of claim 1 further comprising a low pass filter.

6. The system of claim 1 further comprising a difference amplifier.

7. The system of claim 1 further comprising a computer.

8. The system of claim 1 further comprising a photoresistor.

9. The system of claim 1 further comprising a fiber optic cable and a collimator.

10. The system of claim 1 wherein said photo detector comprises two photo diodes.

11. The system of claim 1 wherein said reaction cell is opaque.

* * * * *